United States Patent
Drevik

(10) Patent No.: US 8,715,260 B2
(45) Date of Patent: May 6, 2014

(54) ABSORBENT ARTICLE COMPRISING A DETACHABLE STIFFENING ELEMENT

(75) Inventor: Solgun Drevik, Mölnlycke (SE)

(73) Assignee: SCA Hygiene Products AB, Gothenburg (SE)

(*) Notice: Subject to any disclaimer, the term of this patent is extended or adjusted under 35 U.S.C. 154(b) by 101 days.

(21) Appl. No.: 13/254,723

(22) PCT Filed: Mar. 6, 2009

(86) PCT No.: PCT/SE2009/050237
§ 371 (c)(1),
(2), (4) Date: Sep. 2, 2011

(87) PCT Pub. No.: WO2010/101500
PCT Pub. Date: Sep. 10, 2010

(65) Prior Publication Data
US 2011/0319856 A1    Dec. 29, 2011

(51) Int. Cl.
*A61F 13/15* (2006.01)

(52) U.S. Cl.
USPC .......... 604/385.17; 604/385.18; 604/385.201; 604/358.11; 604/385.101

(58) Field of Classification Search
USPC .......... 604/385.17, 385.18, 385.201, 385.11, 604/385.101
See application file for complete search history.

(56) References Cited

U.S. PATENT DOCUMENTS

| | | | |
|---|---|---|---|
| 6,061,881 A | 5/2000 | Takizawa et al. | |
| 6,171,425 B1 | 1/2001 | Nukina et al. | |
| 6,423,043 B1 | 7/2002 | Gustafsson | |
| 6,543,099 B1 | 4/2003 | Filion et al. | |
| 6,737,147 B2 | 5/2004 | Kennedy et al. | |
| 6,764,477 B1 | 7/2004 | Chen et al. | |
| 6,932,801 B1 | 8/2005 | Samuelsson | |
| 7,156,832 B2 | 1/2007 | Drevik et al. | |
| 2003/0125699 A1 | 7/2003 | Drevik et al. | |
| 2003/0163105 A1 | 8/2003 | Tears et al. | |

(Continued)

FOREIGN PATENT DOCUMENTS

| CN | 1089828 A | 7/1994 |
|---|---|---|
| CN | 201070423 Y | 6/2008 |

(Continued)

OTHER PUBLICATIONS

Chinese Office Action mailed Feb. 28, 2013 issued in corresponding Chinese Patent Application No. 200980157893.8 (14 pages including English translation).

(Continued)

*Primary Examiner* — Jacqueline F. Stephens
(74) *Attorney, Agent, or Firm* — Drinker Biddle & Reath LLP

(57) ABSTRACT

An absorbent article having a longitudinal direction and a transverse direction, a front portion, a rear portion and a crotch portion located between the front portion and the rear portion. The article includes an absorption member having an upper side intended to face a wearer during use of the article and a lower side intended to face away from the wearer during use of the article, and a stiffening element that, at least during use of the article, provides the article with a predetermined shape that enhances the fit of the article to the wearer's body. The stiffening element is secured to the upper side of the absorption member such that an outer side of the stiffening element faces away from the absorption member. The stiffening element includes a material exhibiting mechanical fastening properties on its outer side.

17 Claims, 3 Drawing Sheets

(56) References Cited

U.S. PATENT DOCUMENTS

| | | |
|---|---|---|
| 2004/0260258 A1 | 12/2004 | Hall et al. |
| 2005/0131372 A1 | 6/2005 | Wheeler et al. |
| 2008/0249496 A1 | 10/2008 | Petersen et al. |

FOREIGN PATENT DOCUMENTS

| | | |
|---|---|---|
| CN | 100404012 C | 7/2008 |
| EP | 0 788 785 | 8/1997 |
| EP | 1 395 218 | 2/2006 |
| GB | 2 151 548 | 7/1985 |
| GB | 2 399 378 | 5/2005 |
| JP | H06-502106 | 3/1994 |
| JP | 2008-011932 | 1/2008 |
| RU | 2288685 | 12/2006 |
| RU | 2351300 | 4/2009 |
| WO | WO-93/01783 | 2/1993 |
| WO | WO-93/21879 | 11/1993 |
| WO | WO-94/13239 | 6/1994 |
| WO | 97/22321 | 6/1997 |
| WO | 98/17220 | 4/1998 |
| WO | 98/22061 | 5/1998 |
| WO | WO-98/58614 | 12/1998 |
| WO | 01/17474 | 3/2001 |
| WO | WO 02/087483 A1 | 11/2002 |
| WO | WO-2005/025472 | 3/2005 |
| WO | 2006/038997 | 4/2006 |
| WO | WO-2007/064258 | 6/2007 |
| WO | 2008/093168 | 8/2008 |

OTHER PUBLICATIONS

Notice of Reasons for Rejection dated Apr. 2, 2013 issued in corresponding Japanese patent application No. 2011-552906 (with English translation thereof) (7 pages).

Chinese Office Action dated Apr. 1, 2013 issued in corresponding Chinese patent application No. 200980157896.1 (10 pages including English translation).

Russian Office Action mailed Mar. 19, 2013 issued in Russian Patent Application No. 2011140483, filed Oct. 5, 2011 (7 pages including English translation).

Supplemental European Search Report issued in Application No. EP 09841223.2 on Feb. 20, 2013.

ABSORBENT ARTICLE COMPRISING A DETACHABLE STIFFENING ELEMENT

CROSS-REFERENCE TO PRIOR APPLICATION

This application is a §371 National Stage Application of PCT International Application No. PCT/SE2009/050237 filed Mar. 6, 2009, which is incorporated herein in its entirety.

FIELD-OF THE INVENTION

The present disclosure relates to an absorbent article, such as a sanitary napkin, a panty liner or an incontinence protector, including an absorption member and a stiffening element that, at least during use of the article, provides the article with a certain shape that enhances the fit of the article to the wearer's body.

BACKGROUND

Absorbent articles, such as sanitary napkins, incontinence guards, panty-liners, diapers etc., are known in the art. An important function of absorbent articles is to prevent leakage of body exudates during use of the article. Generally, the article should fit well to the user and stay in place during use. This also enhances the user comfort.

With regard to at least sanitary napkins, incontinence guards and panty-liners, it is previously known to provide the article with stiff or elastic shaping elements that provide the article with a shape that improves the fitting and the ability to stay in place during use. In general, a stiff shaping element has the advantage that the shape of the article is predetermined and maintained during use. On the other hand, stiff shaping elements should be designed with particular care in order not to cause discomfort during use of the article. It is also known to provide the underside of sanitary napkins and similar absorbent articles with fastening means, such as adhesives, for attachment to the user's garments.

WO 0117474 discloses an example of an absorbent article in the form of a sanitary napkin, a panty liner or an incontinence protector, wherein the rear portion of the article includes a longitudinally extending ridge-shaped elevation forming a stiff shaping element that partially extends between the wearer's buttocks during use of the article. This provides good protection against rearward leakage.

WO 98/22061 discloses an absorbent article in the form of a sanitary napkin having stiff front and crotch portions wherein the front portion is curved and inclined upwards, towards the user, with respect to the crotch portion. Further, the article has a narrow waist in the crotch portion allowing a high stiffness without causing discomfort. The desired stiffness is achieved by e.g. including a rigid shape-retaining, spoon-shaped, plastic or metal layer inside the article. The article according to WO 98/22061 is intended to be kept securely and comfortably in position against the body of the user during use, without the need for particular attachment means.

EP 1395218 discloses an adsorbent article in the form of a sanitary towel or incontinence pad including a combined, flat stiffening and absorbent element arranged inside the article, which element gives the article in different regions a predetermined two- or three-dimensional shape (including curvature, bowl-shape and a raised part between the buttocks of the wearer) during use of the article, i.e. when the article is affected by compressive forces generated by the thighs of the wearer. In similarity to WO 98/22061, the front and crotch portions are designed to allow anchoring of the article to thigh muscle tendons, which gives the article a good fit and stability in the fitted position.

Although the known absorbent articles with stiffening elements in many cases provide for a good fit, there still remains a need to further develop this type of absorbent articles.

SUMMARY

It is desired to provide a well-fitting absorbent article, such as a sanitary napkin, that exhibits improved properties compared to conventional absorbent articles with stiff shaping elements. This can be achieved by the disclosed article.

A first aspect relates to an absorbent article, such as a sanitary napkin, a panty liner or an incontinence protector. The article has a longitudinal direction and a transverse direction, a front portion, a rear portion and a crotch portion located between the front portion and the rear portion. The article includes an absorption member having an upper side intended to face a wearer during use of the article and a lower side intended to face away from the wearer during use of the article, and a stiffening element that, at least during use of the article, provides the article with a predetermined shape that enhances the fit of the article to the wearer's body, The stiffening element is secured to the upper side of the absorption member such that an outer side of the stiffening element faces away from the absorption member; and the stiffening element includes a material exhibiting mechanical fastening properties. At least a part of the outer side of the stiffening element exhibits the mechanical fastening properties.

The term absorption member as used herein refers to an item that includes an absorption body for absorption of body fluids. The absorption member may also include e.g. a liquid permeable top sheet arranged on the upper side of the absorption body and a liquid-impermeable back sheet arranged on the lower side of the absorption body.

The term mechanical fastening properties as used herein refers to mechanical fastening means such as hooks, friction adhesives, clips, friction elements and combinations thereof. The fastening means are known, and the fastening means allows for a detachable attachment. Thus, a material exhibiting mechanical fastening properties includes mechanical fastening means of the abovementioned type(s).

The disclosed absorbent article has the advantage that the stiffening element provides the article with a good body fit and at the same time allows an additional, upper/primary, absorption member to be detachably attached on top of the absorption member to which the stiffening element is secured. Thus, the disclosed absorbent article provides a secondary absorption member and a shaping lower part of a two-part absorbent product to which an upper, primary absorption member can be attached. The upper absorption member faces the wearer during use. At least because the stiffening element provides the article with a suitable shape, it is not necessary that the upper absorption member contributes to the shaping of the article. Thereby it becomes possible to use a very flexible upper absorption member, i.e. a very flexible absorption body, which improves the comfort of the absorbent article. Further, it becomes possible to use a simple and non-expensive upper absorption member. This is useful since in many situations only the upper absorption member will be soiled after use of the article, in which situations only the upper absorbent member will need to be disposed and replaced. Thus, in many situations only the non-expensive, upper part of the two-part product needs to be disposed, whereas the more advanced, lower part can be re-used.

Thus, in the inventive absorbent article the stiffening element has a multifunction: shaping and fastening. Such multifunction is generally useful for decreasing the number of components in the absorbent article which makes the manufacture more cost-effective. In the absorbent article disclosed in EP 1395218 multifunction is achieved by providing an absorbent body with a certain stiffness, i.e. stiffening (shaping) and absorbing properties are combined in the same element. However, stiffening and absorbing properties are not easily combined and such a combined element is rather costly. In contrast, the disclosed stiffening (shaping) element is a separate item in relation to the absorption element and instead of combining stiffening and absorbing properties it combines stiffening and fastening properties which are easier to combine. For instance, improvement of the fastening properties of a piece of material does not normally lead to any corresponding impairment of the stiffening properties. Further, because the absorbing function does not have to be taken into account, it is not necessary that the stiffening element has a shape in the lateral plane of the article that is adapted to this function; i.e. the stiffening element secured to the upper side of the absorption member may be e.g. rectangular to avoid or reduce wastage in the production. Because stiffening and fastening properties are easier to combine it becomes possible to manufacture the absorbent article in a more cost-effective way.

In an advantageous embodiment, the material exhibiting mechanical fastening properties also contributes significantly to the stiffness of the stiffening element. This means that the same material provides both the fastening function and, at least a great deal of, the shaping/stiffening function. This way, the structure of the stiffening element can be simplified in that the need for using particular stiffening components or layers is diminished, or even eliminated.

In a further advantageous embodiment, the material exhibiting mechanical fastening properties is a hook material having hooks protruding from the outer side of the stiffening element for fastening to a textile material. Mechanical fasteners in the form of hooks are known in the field of absorbent products to be suitable for attachment to textile materials such as a non-woven material of an upper, primary absorption member. In a particular embodiment, the hook material includes a hook carrier layer to which layer the hooks are secured, wherein the hook material significantly contributes to the stiffness of the stiffening member. Thereby, the hook material provides both the fastening and the stiffening/shaping functions. In a variant of this embodiment, the hook material constitutes the stiffening element. With such a design, no further materials are needed for providing the stiffening element with such functions.

In another advantageous embodiment, the material exhibiting mechanical fastening properties is a friction adhesive material. Thus, the surface of the material exhibits a stickiness that is useful for attaching the stiffening element to e.g. a back sheet of an upper absorption member. Also friction adhesive materials are known to the person skilled in the art. In a variant of this embodiment, the friction adhesive material constitutes the stiffening element. With such a design, no further materials are needed for providing stiffening element with such functions.

The hook material and the friction adhesive material may be combined in that certain parts of the stiffening element can include hook material and other parts can include friction adhesive material. Moreover, the absorbent article can include a plurality of stiffening elements separated from each other, which stiffening elements can include different materials. A further possibility is that the hook carrier material exhibits a stickiness.

In a further advantageous embodiment, the stiffening element exhibits a stiffness that is higher than a part of the absorbent article that surrounds the stiffening element. This has the effect that folding indications are provided along and/or around the stiffening element. These folding indications, together with e.g. the size and geometry of the stiffening element, determine which shape the article will acquire during use. In a particular embodiment, the stiffening element is stiffer than the absorbent member to which it is secured.

In a further advantageous embodiment, the absorbent member includes an absorbent body for absorbing body fluids and a liquid-impermeable back sheet arranged at the lower side of the absorption member. Thus, the back sheet faces away from the wearer and covers the absorbent body in a conventional way.

In a further advantageous embodiment, the absorbent member includes a liquid-permeable top sheet arranged at the upper side of the absorption member, wherein the absorbent body is arranged between the top sheet and the back sheet. In a variant of this embodiment, the stiffening element forms at least a part of the top sheet. In other words, the stiffening element takes the place of the top sheet at some part or parts of the upper side of the absorption member. Thus, it is not necessary to make use of a conventional top sheet that completely covers the upper side of the absorbent member. By using a stiffening element that allows through-flow of bodily fluids, it is possible to allow liquid to flow from an upper absorption member attached to the stiffening element towards the secondary, lower absorption member in the same manner as when using a conventional top sheet. Through-flow of bodily fluids can be achieved by making the stiffening element in a liquid-permeable material and/or by providing the stiffening element with openings.

In a further advantageous embodiment, the article includes an upper, primary absorption member that is detachably attachable to the stiffening element such as to be positioned on top of the absorbent member to which the stiffening element is secured. In a particular embodiment, the absorption member to which the stiffening element is secured extends further in the transversal direction. In a more particular embodiment, the absorption member also extends further in the longitudinal direction, than the upper, primary absorption member.

As used herein a permanent fixation, bond or attachment is a fixation, bond or attachment that is intended to withstand normal use and wear and that cannot be broken without destroying or damaging at least one of the items involved in the fixation. An example of a permanent fixation is the securing of the stiffening element to the upper side of the absorption member. A releasable or detachable join is a bond or attachment that can be broken without damaging or destroying the items involved.

BRIEF DESCRIPTION OF THE DRAWINGS

In the description of embodiments of the invention given below reference is made to the following figures, in which.

DETAILED DESCRIPTION OF PREFERRED EMBODIMENTS

Figure 1:
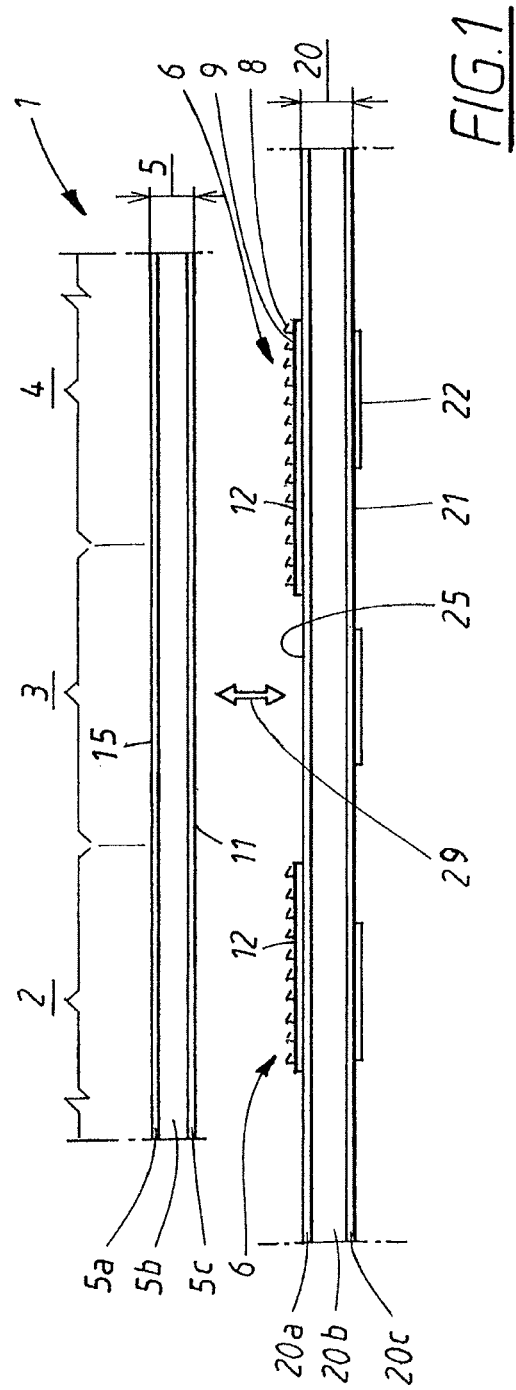
FIG. 1 shows, in a schematic, sectional side view, a first embodiment.

FIG. 1 shows, in a schematic, sectional, cut side view, and in a disassembled state, a first embodiment of an absorbent article 1, in this case a sanitary napkin. The absorbent article 1 has a longitudinal direction, i.e. the left-right direction in FIG. 1, and a transverse direction, i.e. a direction perpendicular to the plane of FIG. 1. Further, the article 1 has a front portion 2, a rear portion 4, and a crotch portion 3 located between the front portion 2 and the rear portion 4. The division of the article 1 into these portions is not strict but describes, in a conventional way, the intended positioning of the article 1 in relation to a wearer.

The absorbent article 1 shown in FIG. 1 includes an upper, primary absorbent member 5, stiffening elements 6 (which in this example are two in number) and a lower, secondary absorption member 20. Each stiffening element 6 is secured to the lower absorption member 20. The upper absorption member 5, which includes an upper side 15 and lower side 11, is, via a lower side 11, detachably attachable to the stiffening elements 6, and thus to the lower absorbent member 20, such as to form a two-part product with two absorption members. In FIG. 1 the absorbent article 1 is disassembled. An arrow 29 indicates that the two absorption members 5, 20 may be detachably attached to each other.

The lower absorption member 20 has an upper side 25 intended to face a wearer during use of the article 1 and a lower side 21 intended to face away from the wearer during use of the article 1. The lower absorption member 20 exemplified in FIG. 1 is in principal structured in a conventional way and includes a liquid-permeable top sheet 20*a*, an absorbent body 20*b* for absorbing body fluids, and a liquid-impermeable back sheet 20*c*. The top sheet 20*a* and the back sheet 20*c* are interconnected around an outer edge of the absorbent body 20*b* such as to form a cover around the absorbent body 20*b* (not shown in FIG. 1).

The lower side 21 of the secondary absorption member 20 is provided with fastening means 22, for instance in the form of adhesives, for attaching the absorbent article 20 to the undergarments of a user. The fastening means 22 are optional.

Suitable materials and material combinations for forming the top sheet 20*a*, the absorbent body 20*b* and the back sheet 20*c* are known. Examples of suitable materials are non-woven fabrics and perforated plastic films for the top sheet 20*a*; cellulose fibers, absorbing foam material and super absorbents (SAP) for the absorbent body 20*b*; and polyethylene film and non-woven fabrics treated with hydrophobing agents for the back sheet 20*c*.

Each of the stiffening elements 6 extends longitudinally and transversely along the upper side 25 of the lower absorption member 20 such that an outer side 12 of the stiffening element 6 faces away from the absorption member 20. The stiffening element 6 is in this example secured to the lower absorption member 20 by being glued to the top sheet 20*a*.

In the example shown in FIG. 1, the stiffening element 6 is entirely made of a hook material including a hook carrier layer (hook substrate) 9 facing and being secured to the absorbent member 5 and further including a plurality of hooks 8 secured to the hook carrier layer 9. The hooks 8 protrude from the hook carrier layer 9, i.e. they protrude from the outer side 12 of the stiffening element 6. Hooks constitute one example of mechanical fasteners that are suitable for detachable attachment to textile materials. Thus, the stiffening element 6 in FIG. 1 is made of a material that exhibits mechanical fastening properties, wherein the outer side 12 of the stiffening element 6 exhibits the mechanical fastening properties. Other mechanical fasteners that may be used are clips or friction elements. Combinations of different types of mechanical fasteners may also be used.

As can be seen in FIG. 1, one of the stiffening elements 6 is positioned in the front portion 2 of the article 1 and the other extends longitudinally from the crotch portion 3 into the rear portion 4. This is similar to what is described in relation to FIG. 3. The purpose of FIG. 1 is, however, only to give a schematic view of the structure of the absorbent article. Different shapes of stiffening elements are described below.

The upper absorption member 5 has a similar structure as the lower absorption member 20, i.e. it includes a liquid-permeable top sheet 5*a*, an absorbent body 5*b* for absorbing body fluids, and a back sheet 5*c*. However, the back sheet 5*c* of the upper absorption member 5 is liquid permeable to allow through-flow of body fluids towards the lower absorbent member 20. The top sheet 5*a* and the back sheet 5*c* are interconnected around an outer edge of the absorbent body 5*b* such as to form a cover around the absorbent body 5*b* (not shown in FIG. 1). In this case the back sheet 5*c* is made of non-woven fabrics which allows for a good attachment to the hooks 8. A back sheet made of e.g. foam or airlaid also allows for a good attachment.

The stiffening element 6 in this example is liquid permeable to allow through-flow of bodily fluids towards the lower absorption member 20.

As can be seen in FIG. 1, the secondary absorption member 20 extends further in the longitudinal direction (i.e. sideways in FIG. 1) than does the primary, upper absorption member 5. The secondary absorption member 20 also extends further in the transversal direction than does the primary, upper absorption member 5. Accordingly, the secondary absorption member 20 surrounds the primary, upper absorption member 5 as seen from above, i.e. the secondary absorption member 20 exhibits a larger area as seen in a direction towards a user of the absorbent article than does the primary, upper absorption member 5. In short, in the example shown, the secondary absorption member 20 is both longer and wider than the upper absorption member 5. This is useful for increasing the leakage protection.

With regard to FIG. 1 it should be noted that it is not necessary that the back sheet 5*c* and the stiffening element 6 are liquid permeable to allow body fluids to be transferred to the secondary absorption member 20. If either or both of the back sheet 5*c* and the stiffening element 6 are liquid impermeable, body fluids may flow transversely (and longitudinally) and pass an outer edge of either or both of these components and then reach the secondary absorption member 20. At least if the back sheet 5*c* is liquid impermeable it is of particular importance that the secondary absorption member 20 is wider, and optionally also longer, than the primary, upper absorption member 5. If the stiffening element 6 has a large area of distribution, it may be equally important that the secondary absorption member 20 is larger. However, the stiffening element 6 may be arranged in the form of narrow strips or bars with openings in-between, or be provided with openings, in order to allow liquid to pass through without requiring the structuring material to be liquid permeable.

After use of the absorbent article 1, it is possible to dispose and replace only the upper absorption member 5, i.e. the lower absorption member 20 can be reused. To avoid unnecessary soiling of the lower absorption member 20 it is useful to provide the upper absorption member 5 with a liquid impermeable back sheet 5*b*.

It may be noted that it is not necessary that the upper absorption member 5 is smaller, i.e. less wide and less long, than the lower absorption member 20. However, a smaller absorption member is sufficient in many situations and since less material is required for manufacturing a smaller absorption member it is a cost-advantage to use a smaller upper absorption member 5. The larger lower absorption member 20 can thus be regarded as an additional, safety member.

Figure 2:
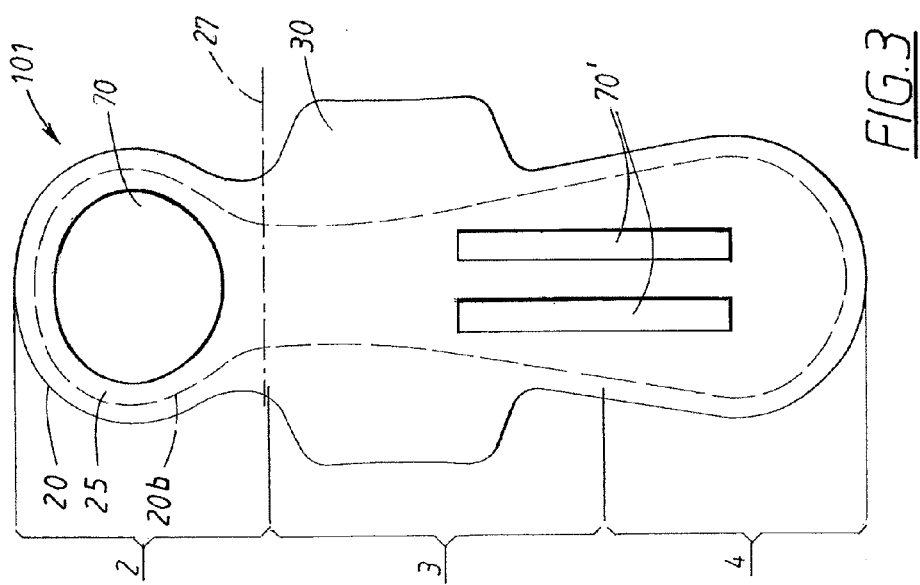
FIG. 2 shows the top side of an adsorbent article according to another embodiment.

Suitable hook materials for the embodiments shown in FIGS. 1 and 2 are available as KHK0002 or CHK 00752 from 3M Company. These materials have a suitable stiffness for giving the article 1 a good shape during use and provides for a good attachment.

The hooks 8 can, of course, be chosen such as to be adapted to the intended use. That is, the hooks 8 can be adapted to interact particularly well with a certain type of material at the lower side 11 of the upper absorption member 5.

As an alternative to the hook material described above, the stiffening element 6 can, at least partly, be made of a friction adhesive material, i.e. of a material that exhibits a stickiness that can be used to mechanically fasten the stiffening element 6 to the upper absorption member 5. In such a case, the back sheet 5c of the primary absorption member 5 can be made of e.g. a nonwoven material or a perforated plastic film which allows for a good attachment to the friction adhesive material.

Friction adhesive materials, which also are referred to as friction materials, should not be confused with conventional fastening adhesives. A general difference between these materials is that the pressure sensitive adhesive of conventional fastening material does provide reasonable tack, peel and shear after a bond has been initiated by putting pressure onto the system. Different to such a behavior, a friction adhesive material will mainly provide shear. This shear or friction is proportional to the force used to press the friction material onto a second surface. After release of the pressure the system will show basically no remaining tack, peel or friction.

An example of a suitable friction adhesive material is 5401 Traction Tape available from 3M Company.

Hook material and friction adhesive material may be combined in the absorbent article 1 in that some parts of the stiffening element 6 (or some of the stiffening elements, if a plurality is present) includes hook material and some includes friction adhesive material. It is also possible to use a material that has both properties, for instance a hook material that exhibits a stickiness.

The stiffening element is sufficiently stiff for, as far as possible, preventing the absorbent article from being compressed or otherwise deformed in an uncontrolled manner during use of the article.

The stiffening element 6 should exhibit a stiffness that is higher than the material of the absorbent article 1 that surrounds the stiffening element. In relation to the embodiment described here, this means that the stiffening element 6 should be stiffer than the (lower) absorbent member 20. That the stiffness of the stiffening element 6 is higher than its surroundings has the effect that folding indications are provided along and/or around the stiffening element 6. These folding indications, together with e.g. the size and geometry of the stiffening element 6, determine which shape the article 1 will acquire during use.

In particular embodiments, the stiffening element 6 exhibits a stiffness in a dry state in the order of 1-15 N as measured according to ASTM D 4032-82.

The stiffening elements can have a variety of shapes and positions depending on the shape desired. Various advantageous shapes of absorbent articles are known. In any case, the stiffening element(s) can be arranged to, at least during use of the article, provide the article with a certain, predetermined shape that enhances the fit of the article to the wearer's body. A stiffening element may have a flat form before use but take a three-dimensional shape upon use of the article, i.e. when the article is affected by compressive forces generated by the thighs of the wearer. Alternatively, a stiffening element may have a three-dimensional shape already before use of the article.

In particular embodiments, the stiffening element(s) 6 can be arranged such as to, at least during use of the article, provide the article with one or several of the following shapes:

A width H at a transition 27 (see FIG. 2) between the crotch portion 3 and the front portion 2 that is less than the width at the front portion 2. This allows anchoring of the article to/between the thigh muscle tendons of the user and prevents the article from moving backwards during use. In particular embodiments, the width H is in the range of 15-45 mm.

A three-dimensional bowl-like shape in an area in the front portion 2. This enhances the body fit.

A ridge-shaped elevation that partially extends between the wearer's buttocks during use of the article. This prevents rearward leakage.

A raised portion (hump) intended to make contact with the genitals of the wearer during use of the article. This provides for better absorption of bodily fluids.

Figure 3:
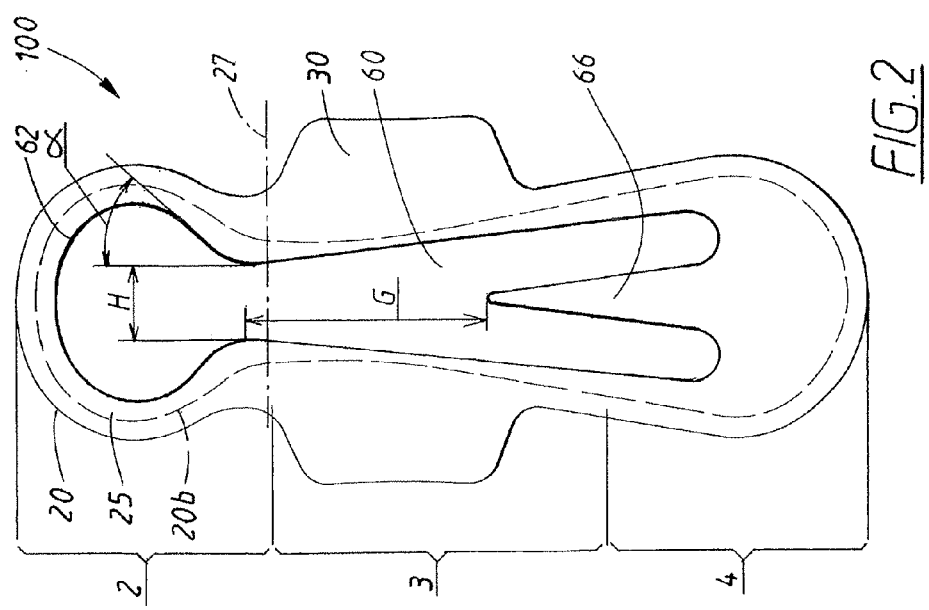
FIG. 3 shows the top side of an adsorbent article according to yet another embodiment.
Figure 4:
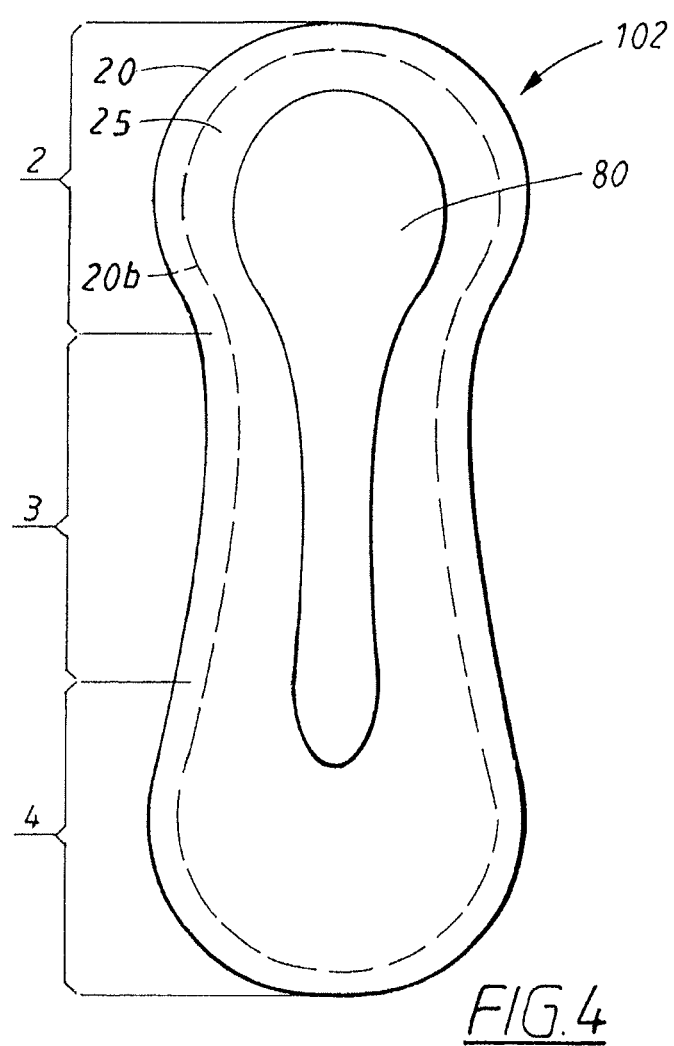
FIG. 4 shows the top side of an adsorbent article according to still another embodiment.

FIGS. 2-4 show absorbent articles as seen from above with the main purpose of showing examples of geometries of the stiffening element(s) 6. Thus, the upper side 25 of the (lower) absorption member and the outer side 12 of the stiffening element face upwards in these figures. Any upper absorption members are not shown. The position of the absorbent body 20b is indicated with a dashed line.

FIG. 2 shows an absorbent article 100 with a first example of a suitable shape of a stiffening element 60. In this example, the stiffening element 60 is flat and has a shape similar to what is shown in EP 1395218. A peripheral edge of the stiffening element 60 is indicated by the reference number 62.

Main features of the stiffening element 60, besides the flatness, are inter alfa: i) that it extends in the longitudinal direction of the article 100 over the crotch portion 3 and at least some way in over the front portion 2; ii) that it has a width H at the transition 27 between the crotch and front portions 3, 2 that is within the range of 15-45 mm; iii) that it has a length G in the crotch portion 3 within the range of 70-120 mm; iv) that the side edges of the stiffening element 60, in the direction from the crotch area in over the front portion 2, form an acute angle α (i.e. <90°, preferably 35-55°) with a line in the longitudinal direction of the article 100; and v) that it also extends some way in over the rear portion 4 and has a wedge-shaped cutout 66 extending from a rear end edge of the stiffening element 60 in a direction towards the crotch portion 3, as a result of which the product is, during use, imparted with a fold along the longitudinal direction of the article 100 in the cutout 66. The fold extends into the cleft between the buttocks of the wearer during use of the article 100. These features all contribute to the fit of the article to the wearer during use. One or several of these features may be used to enhance the fit of the article.

FIG. 3 shows, in a schematic view, an absorbent article 101 with a second example of a suitable shape of a stiffening element. In this case, the stiffening element includes three parts; one front element 70 located in the front portion 2 and two rear, elongated elements 70' that extend in parallel in the longitudinal direction in part of the rear portion 4 and part of the crotch portion 3 of the article 101. In the example shown, the rear elements 70' are rectangular in order to simplify production and avoid wastage. Of course, these elements may be more or less rounded off such as to increase comfort (avoid chafe). Also the front element 70 may be rectangular, and perhaps rounded off, to simplify production and avoid wastage. The front element provides a three-dimensional bowl-like shape in an area in the front portion 2. The rear elements provide a fold in the longitudinal direction of the article 101 in similarity to the rear part of the stiffening element shown in FIG. 2. In the example shown in FIG. 3, an absence of stiffening elements in the transition zone 27 between the front and crotch portions 2, 3 provides for a suitable width of the article 101 in this position.

As shown in FIGS. 2 and 3, the absorption article 100, 101 may be provided with fastening wings 30 provided with adhesives (not shown in the figures) for enhanced attachment of the article to the undergarments of the wearer. Such wings are known.

FIG. 4 shows, in a schematic view, an absorbent article 102 with a third example of a suitable shape of a stiffening element 80. In this case the stiffening element 80 has the shape of a spoon with a three-dimensional bowl-shaped part located in the front portion 2 and a more narrow part extending longitudinally and centrally over the crotch portion 3, where a hump is formed, and somewhat into the rear portion 4 as to produce a rearward leakage protection as described above.

The invention is not limited by the embodiments described above but can be modified in various ways within the scope of the claims. For instance, the stiffening element 6, 60, 70, 70', 80, irrespective of whether it includes hook material, friction adhesive material, or a combination thereof, does not necessarily have to be made entirely of this or these materials. The stiffening element may e.g. include layers of different materials that together build up the total stiffness. What is important is that the stiffness is sufficient for giving the absorbent article a suitable, predetermined shape during use, and that the outer side of the stiffening element exhibits mechanical fastening properties.

The absorbent article 1, 100, 101, 102 may or may not include the upper absorption member 5 shown in FIG. 1. The upper and lower absorption members 5, 20 may be packaged or sold separately and be assembled by a user prior to use. Either or both of the upper and lower absorption members 5, 20 can be provided with markers for proper positioning of the upper absorption member 5 onto the lower absorption member 20. For instance, the upper side 25 of the lower absorption member 20 can be provided with a marker in the form of a line corresponding to an outer edge of the upper absorption member 5.

The stiffening element 6, 60, 70, 70', 80 may be articulated for increasing longitudinal flexibility of the article. "Hinges" for this purpose can be arranged in the form of longitudinally distributed slits or hook-free regions if the piece of material making up the stiffening element includes a hook material.

Foam is an example of a material useful for forming the stiffening element 6, 60, 70, 70', 80.

The stiffening element 6, 60, 70, 70', 80 can be secured to the upper side 25 of the absorption member 20 by means of e.g. adhesives and/or treatment by ultrasonic waves, heat or laser.

The lower, secondary absorption member 20 may be arranged to be capable of absorbing larger volumes of fluids and thereby be suitable for handling of urination, or it could be arranged to be capable of absorbing only small volumes of fluids, a few ml, and thereby mainly work as an additional, safety absorption member. Of course, it can also be arranged to be capable of absorbing fluid volumes that are between "larger" and "small".

The invention claimed is:

1. An absorbent article having a longitudinal direction and a transverse direction, a front portion, a rear portion, and a crotch portion located between the front portion and the rear portion, said article comprising:
    an absorption member having an upper side intended to face a wearer during use of the article and a lower side intended to face away from the wearer during use of the article, and
    a stiffening element that, at least during use of the article, provides the article with a predetermined shape that enhances the fit of the article to the wearer's body,
    wherein the stiffening element is secured to the upper side of the absorption member such that an outer side of the stiffening element faces away from the absorption member, and the stiffening element comprises a material exhibiting mechanical fastening properties,
    wherein at least a part of the outer side of the stiffening element exhibits said mechanical fastening properties, and
    wherein the stiffening element that is arranged on the upper side of the absorption member includes a wedge-shaped cutout extending form a rear end edge in a direction towards the crotch portion.

2. The absorbent article according to claim 1, wherein the material exhibiting mechanical fastening properties also contributes to the stiffness of the stiffening element.

3. The absorbent article according to claim 1, wherein the material exhibiting mechanical fastening properties is a hook material having hooks protruding from the outer side of the stiffening element.

4. The absorbent article according to claim 3, wherein the hook material comprises a hook carrier layer to which the hooks are secured, and wherein the hook material contributes to the stiffness of the stiffening member.

5. The absorbent article according to claim 4, wherein the hook material constitutes the stiffening element.

6. The absorbent article according to claim 1, wherein the material exhibiting mechanical fastening properties is a friction adhesive material.

7. The absorbent article according to claim 6, wherein the friction adhesive material constitutes the stiffening element.

8. The absorbent article according to claim 1, wherein the stiffening element exhibits a stiffness that is higher than a part of the absorbent article that surrounds the stiffening element.

9. The absorbent article according to claim 1, wherein the stiffening element is stiffer than the absorption member.

10. The absorbent article according to claim 1, wherein the absorption member includes an absorbent body for absorbing body fluids and a liquid-impermeable back sheet arranged at the lower side of the absorption member.

11. The absorbent article according to claim 10, wherein the absorbent member comprises a liquid-permeable top sheet arranged at the upper side of the absorption member, and wherein the absorbent body is arranged between the top she and the back sheet.

12. The absorbent article according to claim 11, wherein the stiffening element forms at least a part of the top sheet.

13. The absorbent article according to claim 1, wherein the article further comprises an upper absorption member that is detachably attachable to the stiffening element such as to be positioned on top of the absorption member to which the stiffening element is secured.

14. The absorbent article according to claim 13, wherein the absorption member to which the stiffening element is secured extends further in the transversal direction than the upper absorption member.

15. The absorbent article according to claim 14, wherein the absorption member to which the stiffening element is secured also extends further in the longitudinal direction than the upper absorption member.

16. The absorbent article according to claim 1, wherein the stiffening element is arranged to allow through-flow of body fluids.

17. The absorbent article according to claim 1, wherein the stiffening element that is arranged on the upper side of the absorption member includes a circular portion arranged in the front portion.

* * * * *